United States Patent
Winters et al.

[11] Patent Number: 5,836,310
[45] Date of Patent: Nov. 17, 1998

[54] PATIENT SUPPORTING GATE VEST

[76] Inventors: Ramona M. Winters; Dorothy F. Hyde, both of 2730 Highway 73 South, Nekoosa, Wis. 54457

[21] Appl. No.: 886,500
[22] Filed: Jul. 1, 1997
[51] Int. Cl.⁶ .................................................. A61G 15/00
[52] U.S. Cl. ........................ 128/845; 128/846; 128/874; 2/102
[58] Field of Search ................................. 128/869, 873, 128/874, 875, 876, 845, 846; 269/484, 485; 2/94, 102; 602/19

[56] References Cited

U.S. PATENT DOCUMENTS

| 970,824 | 9/1910 | Hoppenstein | 2/102 |
|---|---|---|---|
| 3,028,200 | 4/1962 | Dye | 297/484 |
| 4,330,152 | 5/1982 | Legan | 297/484 |
| 4,429,419 | 2/1984 | Snyder | 2/102 |
| 5,397,171 | 3/1995 | Leach | 128/875 |
| 5,544,363 | 8/1996 | McCue | 2/102 |

Primary Examiner—Michael A. Brown
Attorney, Agent, or Firm—Henry S. Miller

[57] ABSTRACT

The invention is a vest formed from mesh material for assisting ambulatory patients move about. The vest is formed of a single piece of material with a hole in the center for the head and recesses that form arm holes when the material is folded over the body creating a front and back panel. The panels are connected under the arm holes with zippers or other material consistent with a zipper closure. The back panel contains a pair of straps attached at a diagonal to the shape of the back and intersect near the center point of the panel. A pair of handles of web or other strong material are vertically mounted proximate the center point to the straps, thereby allowing a high degree of control over the torso of the patient.

8 Claims, 2 Drawing Sheets

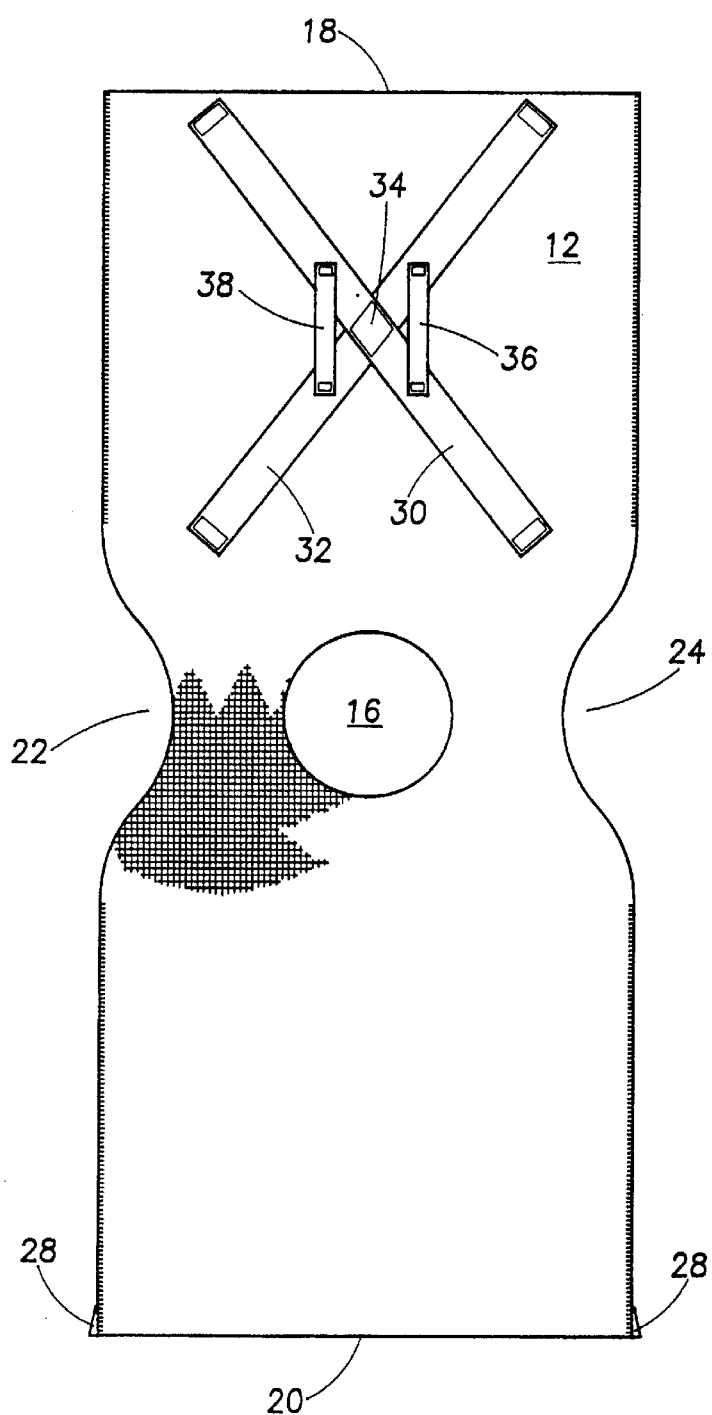
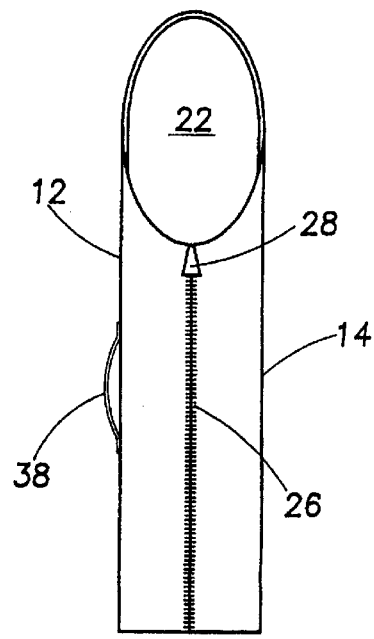

PATIENT SUPPORTING GATE VEST

BACKGROUND OF THE INVENTION

1. Field of the Invention

The invention relates generally to a garment for ambulatory patients and more specifically to a vest for aiding a patient to move safely about.

2. The Problem and Relevant Prior Art

The gate belt is a standard nursing home tool to aid in the assistance of ambulatory patients to move about. The belt is a bit wider than a normal dress belt and made of a heavy cotton material. When worn by a patient, a health care worker is able to grasp the belt from behind and steady those with an unstable gate or prevent a traumatic collapse should the patient fall, faint or otherwise lose balance.

The gate belt, because of its narrow engagement with the patients torso can be dangerous for very heavy and the very small, frail patients, exerting excessive forces on the sternum and rib cage, including causing fractures to both.

The patient vest has been limited in its usefulness with the elderly due to the degree of difficulty in applying the garment to the patient. Many patients are unable to articulate their limbs to a degree where a vest may be worn. In addition a conventional vest lacks any means for a health care worker to grasp in order to stabilize a patient. Therefore, in the past the vest has not been available for the stabilization of ambulatory patients.

U.S. Patents that show the state of the art and disclose relevant garments for use in health care situations include: U.S. Pat. No. 4,159,010 issued Jun. 26,1979 to Mitro who discloses a lifting vest for disabled patients; U.S. Pat. No. 4,488,544 issued Dec. 18, 1984 to Triunfol for a body restraint shirt for controlling patients movements; U.S. Pat. No. 4,981,307 issued Jan. 1, 1991 to Walsh for a waist engaging suspension harness for lifting patients; U.S. Pat. No. 5,097,535 issued Mar. 24, 1992 to Dye et al. who disclose a garment that opens along the legs and arms and in other important locations for medical examination, and U.S. Pat. No. 5,097,536 issued Mar. 24, 1992 to Cohen for a medical examination shirt that opens for modest examination of the breast.

The prior art cited, taken alone or in combination fails to anticipate the instant invention. The invention as disclosed and claimed herein provides distinct and useful advantages not previously known to the prior art.

SUMMARY OF THE INVENTION

The invention combines the principals of the gate belt and a restraint vest to provide a garment that will allow a health care worker to safely aid an ambulatory patient to move about. The invention is designed to provide a snug fit for the patient, therefore it is made in a variety of sizes. The body of the invention consists of a single piece of nylon mesh material containing a central aperture through which a patient places his head. The material is then draped over the patients torso, front and rear, and the edges are connected under the arms. Areas, proximate the aperture are recessed to allow for the arms of the patient to pass through. The edges are connected by a zipper beginning at the waist and ending under the armpit. The front panel is without relief while the back panel includes a pair of straps sewn diagonally and intersecting at the proximate center point of the panel. Connected to the straps at opposed sides but proximate the center point are vertical handles formed of a strong cotton strapping material.

In use, the vest is applied to the patient and as he perambulates the health care worker is able to maintain control of the upper torso thereby preventing a forward fall and controlling the descent in the event of a direct vertical fall.

It is therefore an object of the invention to provide a new and improved patient supporting gate vest.

It is another object of the invention to provide a new and improved patient supporting gate vest that is safer for the patient than any existing similar known device.

It is a further object of the invention to provide a new and improved patient supporting gate vest that is easily applied to patients with an infirmity.

It is still another object of the invention to provide a new and improved patient supporting gate vest that provides more control over the movements of the patient than any known similar device.

It is still a further object of the invention to provide a new and improved patient supporting vest which maybe easily and efficiently manufactured and marketed.

It is another object of the invention to provide a new and improved patient supporting vest which is of a durable and reliable construction.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a top plan view of the invention in the open condition.

FIG. 5 is a side elevation view of the invention.

DETAILED DESCRIPTION OF A PREFERRED EMBODIMENT

Figure 1:
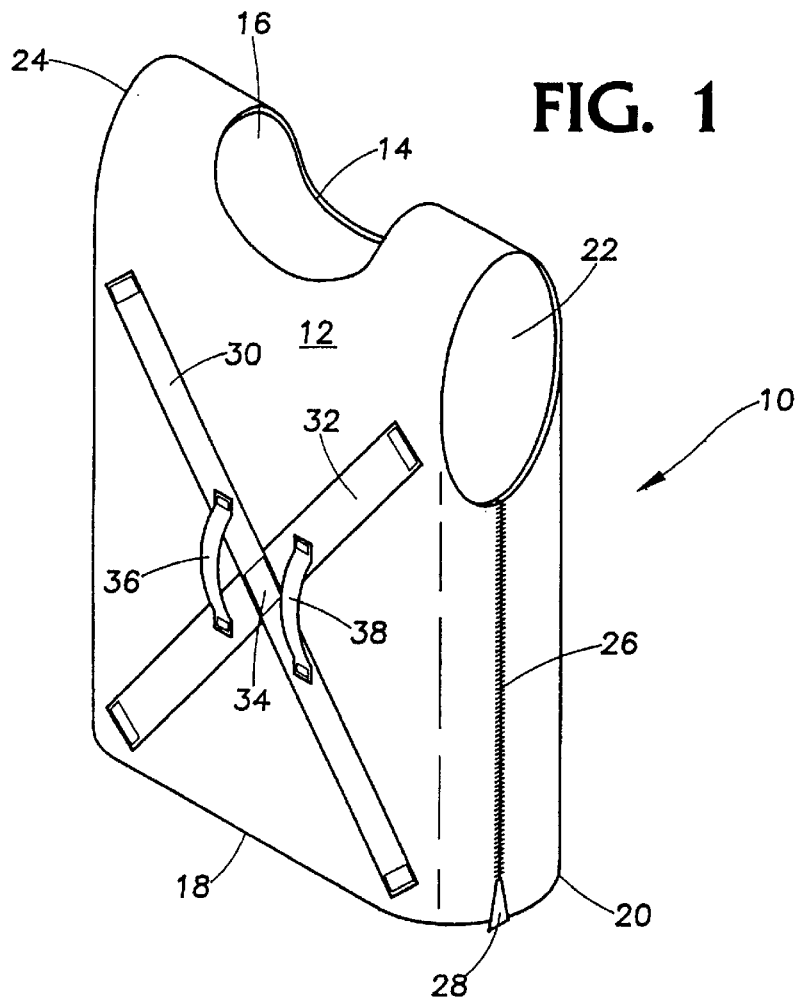
FIG. 1 is a perspective view of the invention.
Figure 3:
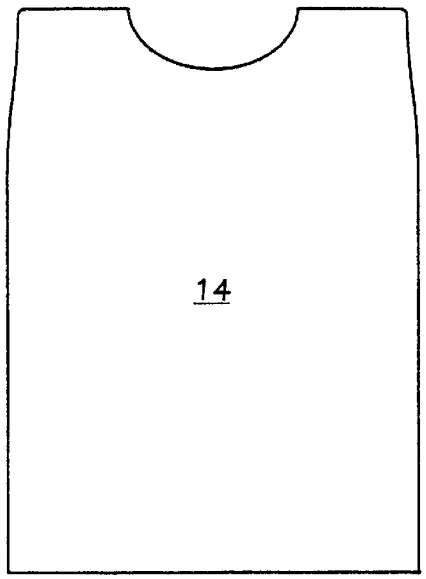
FIG. 3 is an elevation view of the front panel of the invention.
Figure 4:
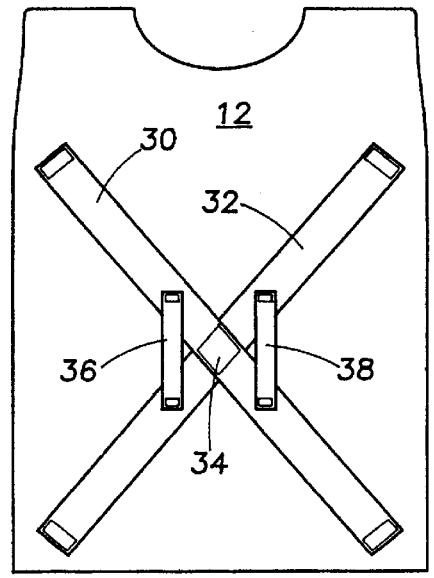
FIG. 4 is an elevation view of the back panel of the invention.

Referring now to the Figures, the invention is shown generally at 10 and consists of a single piece of mesh material which may be cotton, nylon or other material, which is folded over to form a back panel 12 and a front panel 14. An aperture 16 lies midway between the ends 18,20 of the material. Along the edges of the material proximate the aperture are recesses 22,24 which form arm openings when the material is folded over and joined. The front and back panels are joined under the arm hole by a hook and loop material or a zipper 26 which begins closing with the slider 28 at the end of the material 18,20 and ending at the arm hole 22. In the alternative hook (25) and loop (27) material may be substituted for the zipper 26.

The back panel 12 includes a pair diagonally placed reinforcing straps 30,32 which are sewn to the mesh material. A corresponding securing strap material may be located on the opposed side of the material as is well known in the art for purposes of strengthening the attachment. The straps cross at the proximate center point of the back panel 34 to provide for better control of the patient in the event of a misstep or fall.

A pair of heavy cotton, nylon or web material handles 36,38 are attached in a spaced relation with parallel vertical axis, to straps 30,32. The straps are so placed that they will allow two persons to assist the patient, one person using a handle on either side of the patient or if required one person could grasp both straps to control the movement of the patient.

The preferred method of attachment for the parts of the invention is by stitching with a quality nylon thread although other methods of attachment known in the prior art are not excluded.

It should be understood, of course, that the foregoing disclosure relates to only a preferred embodiment of the invention and that numerous modifications or alterations may be made therein without departing from the spirit and scope of the invention as set forth in the appended claims.

What is claimed is:

1. A single piece upper body garment having a centrally located aperture for receiving the head of the wearer, and aligned, opposed recessed areas for accepting the arms of the wearer;

means for releasibly joining the edges along each of two sides for forming a vest like garment, having a front panel and a back panel;

a first back panel reinforcing strip extending diagonally across the surface of the panel;

a second back panel reinforcing strip extending diagonally across the surface of the panel transversely intersecting the first reinforcing strip;

a pair of parallel, space apart handles attached to the first and second reinforcing strips and affording a means for stabilizing or supporting a person wearing the garment, from behind.

2. A single piece upper body garment according to claim 1 wherein: the means for joining the edges of the garment is hook and loop material.

3. A single piece upper body garment according to claim 1 wherein: the means for joining the edges of the garment is a zipper.

4. A single piece upper body garment according to claim 3 wherein: the first back panel reinforcing strip extends from the region of the left shoulder to the region of the right hip, and the second back panel reinforcing strip extends from the region of the right shoulder to the region of the left hip, and the first and second strips cross in the region of the center of the back of the wearer.

5. A single piece upper body garment according to claim 4 wherein: the pair of handles are formed from the web strap material.

6. A single piece upper body garment according to claim 5 wherein: the web strap material is nylon.

7. A single piece upper body garment according to claim 6 wherein: the garment is formed from a mesh material.

8. A single piece upper body garment according to claim 7 wherein: the mesh material is nylon.

\* \* \* \* \*